United States Patent [19]

Hester, Jr.

[11] 4,455,307

[45] Jun. 19, 1984

[54] ANTIHYPERTENSIVE USE OF TRIAZOLOBENZODIAZEPINES

[75] Inventor: Jackson B. Hester, Jr., Comstock Township, Kalamazoo County, Mich.

[73] Assignee: The Upjohn Company, Kalamazoo, Mich.

[21] Appl. No.: 455,780

[22] Filed: Jan. 5, 1983

Related U.S. Application Data

[63] Continuation-in-part of Ser. No. 336,814, Jan. 4, 1982, abandoned.

[51] Int. Cl.$^3$ .................. A61K 31/55; C07D 487/04
[52] U.S. Cl. .................. 424/246; 260/243.3; 260/244.9; 260/245.5; 424/248.4; 424/248.5; 424/248.52; 424/248.58; 424/250; 424/263; 424/267; 424/269
[58] Field of Search ............... 260/243.3, 245.5, 244.4; 424/246, 248.4, 248.5, 248.52, 248.58, 250, 263, 267, 269

[56] References Cited

U.S. PATENT DOCUMENTS

| | | | |
|---|---|---|---|
| 3,646,055 | 2/1972 | Hester, Jr. | 260/308 C |
| 3,709,899 | 1/1973 | Hester, Jr. | 260/308 R |
| 3,734,922 | 5/1973 | Hester, Jr. | 260/296 T |
| 3,751,426 | 8/1973 | Hester, Jr. | 260/308 R |
| 3,767,660 | 10/1973 | Hester, Jr. | 260/294.9 |
| 3,786,149 | 1/1974 | Collins | 424/269 |
| 3,803,315 | 4/1974 | Collins | 424/269 |
| 3,821,388 | 6/1974 | Collins | 424/269 |
| 3,836,660 | 9/1974 | Collins | 424/269 |
| 3,836,661 | 9/1974 | Collins | 424/269 |
| 3,840,664 | 10/1974 | Collins | 424/269 |
| 3,856,802 | 12/1974 | Szmuszkovicz | 260/296 T |
| 3,864,356 | 2/1975 | Meguro et al. | 260/308 C |
| 3,865,811 | 2/1975 | Meguro et al. | 260/239 BD |
| 3,870,706 | 3/1975 | Allgeier et al. | 260/239.3 T |
| 3,880,877 | 4/1975 | Sellstedt et al. | 260/308 R |
| 3,882,101 | 5/1975 | Sellstedt | 260/239 BD |
| 3,886,174 | 5/1975 | Hester, Jr. | 260/308 R |
| 3,891,666 | 6/1975 | Hester, Jr. | 260/308 B |
| 3,894,025 | 7/1975 | Hester, Jr. | 260/268 TR |
| 3,912,753 | 10/1975 | Hester, Jr. | 260/308 R |
| 3,987,052 | 10/1976 | Hester, Jr. | 260/308 R |
| 3,996,230 | 12/1976 | Hester, Jr. | 260/268 TR |
| 4,000,289 | 12/1976 | Collins | 424/269 |
| 4,141,902 | 2/1979 | Hester, Jr. | 260/308 R |

FOREIGN PATENT DOCUMENTS

51-6994  1/1976  Japan .
1323277  7/1973  United Kingdom .
1331015  9/1973  United Kingdom .

OTHER PUBLICATIONS

The Merck Veterinary Manual, 5th Ed., Merck and Co., Rahway, N.J., 1979, p. 59.
Comer and Matier In Burger's Medicinal Chemistry, 4th Ed., Part III, John Wiley and Sons Inc., New York, 1981, pp. 285–337.
Chai et al., J. Pharm. Exp. Ther. 154:271 (1966).
Anonymous, Med. Lett. Drug Therap. 16:96 (1974).
Whitehead, et al., Biol. Psych. 12:597 (1977).
D. Kelly, "Clinical Experience with Benzodiazepines in Psychosomatic Disorders," In R. G. Priest et al., Eds., Benzodiazepines Today and Tomorrow, University Park Press, Baltimore, Md. 1980, pp. 99–112.
Rudzik and Kamdar, J. Med. Chem. 14:1078 (1971).
Hester and VonVoigtlander, J. Med. Chem. 22:1390 (1979).
Hester, Rudzik and VonVoigtlander, J. Med. Chem. 23:392 (1980).
Hester, Rudzik and VonVoigtlander, J. Med. Chem. 23:402 (1980).

*Primary Examiner*—Richard Raymond
*Attorney, Agent, or Firm*—Lawrence T. Welch; Robert A. Armitage; William G. Scanlon

[57] ABSTRACT

This specification concerns the use to treat hypertension in mammals of novel and known 4H-s-triazolo[4,3-a][1,4]benzodiazepines, known 4H-s-triazolo[4,3-a][1,3,4]benzotriazepines and 2,4-dihydro-2-alkyl-1H-s-triazolo[4,3-a][1,4]benzodiazepin-1-ones, and novel 2,4-dihydro-2-alkyl-1H-s-triazolo[4,3-a][1,4]benzodiazepin-1-thiones.

18 Claims, No Drawings

ANTIHYPERTENSIVE USE OF TRIAZOLOBENZODIAZEPINES

CROSS REFERENCE TO RELATED APPLICATIONS

This application is a continuation-in-part of application Ser. No. 336,814, filed Jan. 4, 1982, now abandoned.

DESCRIPTION

Technical Background

The present invention relates to a novel method of use for known compounds. The present invention also relates to novel compounds and their use in the same method of use discovered for the known compounds.

In particular, the invention relates to the novel method of lowering the blood pressures of mammals, including humans, by administration thereto of sufficient amounts of certain known and novel 4H-s-triazolo[4,3-a][1,4]benzodiazepines, certain known 4H-s-triazolo[4,3-a][1,3,4]-benzotriazepines and 2,4-dihydro-2-alkyl-1H-s-triazolo[4,3-a][1,4]-benzodiazepin-1-ones, and certain novel 2,4-dihydro-2-alkyl-1H-s-triazolo[4,3-a][1,4]benzodiazepin-1-thiones, or pharmacologically acceptable acid addition salts thereof.

The invention concerns, therefore, a method of treating hypertension in mammals, including humans.

The invention also concerns novel 1-thiomorpholino-4H-s-triazolo[4,3-a][1,4]-benzodiazepines, 1-azetidino-4H-s-triazolo[4,3-a][1,4]benzodiazepines, and 2,4-dihydro-2-alkyl-1H-s-triazolo[4,3-a][1,4]benzodiazepin-1-thiones, and their pharmacologically acceptable acid addition salts.

Hypertension is a disease characterized by pathologically elevated, systemic arterial blood pressure. Hypertension in humans and agents for treating the disease have recently been reviewed by Comer and Matier in Burger's Medicinal Chemistry, 4th Ed., Part III, John Wiley and Sons Inc., New York, 1981, pp. 285-337. Hypertension is also known to occur in non-human mammals. See, e.g., the Merck Veterinary Manual, 5th Ed., Merck and Co. Rahway, N.J., 1979, p. 59.

Ill effects caused or exacerbated by hypertension, in humans as well as other mammals, include renal insufficiency and failure, stroke, cardiac insufficiency and failure, and increased risks of coronary and cerebral atherosclerosis and the untoward consequences thereof. By reducing the blood pressure of a mammal suffering from hypertension, the ill effects of the disease can be prevented, ameliorated, or eliminated.

Numerous methods and agents for reducing blood pressure in mammals are known. Methods and agents for reducing hypertension in humans are reviewed in the Comer and Matier reference cited above. Most methods and agents effective for reducing hypertension in humans are also effective for reducing blood pressure in non-human mammals, including those suffering from hypertension. Indeed, the usefulness of a method or agent for treating hypertension in humans is usually first indicated by its blood-pressure lowering effect in non-human mammals.

Numerous agents active in the central nervous system are known to be antihypertensives. Many of these centrally acting agents are also active as hypnotics, sedatives, tranquilizers, or muscle relaxants. See the Comer and Matier chapter, cited above, at pages 292-302.

There are indications that non-triazole-ring-bearing benzodiazepines, such as diazepam and bromazepam, which are active through the central nervous systems of mammals as, among others, tranquilizers, muscle relaxants, sedatives, anxiolytics or anticonvulsants, might also be active as antihypertensives in mammals. See Chai et al., J. Pharm. Exp. Ther. 154, 271 (1966); Anonymous, Med. Lett. Drug Therap. 16, 96 (1974); Whitehead et al., Biol. Psych. 12, 597 (1977); D. Kelly, "Clinical Experience with Benzodiazepines in Psychosomatic Disorders," in R. G. Priest et al., eds., Benzodiazepines Today and Tomorrow, University Park Press, Baltimore, Md., 1980, pp. 99-112.

Known compounds of concern in the present specification are disclosed in Hester, Rudzik and Kamdar, J. Med. Chem. 14, 1078 (1971); Hester and VonVoigtlander, J. Med. Chem. 22, 1390 (1979); Hester, Rudzik and VonVoigtlander, J. Med. Chem. 23, 392 (1980); and Hester, Rudzik and VonVoigtlander, J. Med. Chem. 23, 402 (1980); in the following U.S. Pat. Nos. 3,646,055; 3,709,899; 3,734,922; 3,751,426; 3,767,660; 3,856,802; 3,870,706; 3,880,877; 3,882,101; 3,886,174; 3,891,666; 3,894,025; 3,912,753; 3,987,052; 3,996,230; and 4,141,902; and in Belgian Pat. No. 782,680.

The known compounds are disclosed to be active as sedatives, tranquilizers and muscle-relaxants in mammals and birds. See U.S. Pat. Nos. 3,646,055; 3,734,922; 3,751,426; 3,767,660; 3,856,802; 3,880,877; 3,882,101; 3,886,174; 3,891,666; 3,894,025; 3,912,753; 3,987,052; 3,996,230; 4,141,902; see also Belgian Pat. No. 782,680.

The known compounds wherein the substituent at the 6-position is 2-pyridyl have additionally been disclosed to be hypnotics and anticonvulsants in birds and mammals. See U.S. Pat. Nos. 3,734,922 and 3,767,660. Several of the known compounds are known to possess anxiolytic activity in mammals. See U.S. Pat. Nos. 3,894,025; 3,912,753; and 3,996,230; and Hester, Rudzik and Kamdar; Hester and VonVoigtlander, and both Hester, Rudzik and VonVoigtlander references, all cited above. The known 2,4-dihydro-2-alkyl-1H-s-triazolo[4,3-a][1,4]benzodiazepin-1-ones have been disclosed to have anti-aggressive-behavior effects in mammals and birds. See U.S. Pat. No. 3,646,055. See also U.S. Pat. No. 3,865,811, which discloses that 2,4-dihydro-1H-s-triazolo[4,3-a][1,4]benzodiazepin-1-ones and -1-thiones unsubstituted at the nitrogen atom at position 2 are anticonvulsants and sleep-inducers in mammals. The 1-(4-methyl-1-piperazinyl)-4H-s-triazolo[4,3-a][1,4]benzodiazepines, 1-morpholino-8-chloro-6-phenyl-4H-s-triazolo[4,3-a][1,4]benzodiazepine and 1-pyrrolidino-8-chloro-6-phenyl-4H-s-triazolo[4,3-a][1,4]benzodiazepine display antidepressant activity in mammals. U.S. Pat. Nos. 3,894,025 and 3,996,230; Hester and VonVoigtlander, cited above; Hester, Rudzik and VonVoigtlander, J. Med. Chem. 23, 392 (1980). 1-Aminoalkyloxy- and 1-aminoalkylthio-4H-s-triazolo[4,3-a][1,4]benzodiazepines have been disclosed to be hypnotics and anticonvulsants in mammals and birds. U.S. Pat. No. 3,912,753. 1-alkoxymethyl and 1-hydroxymethyl-4H-s-triazolo[4,3-a][1,4]benzodiazepines have been disclosed to inhibit somatic reflexes and have depressant, including anticonvulsant and anti-aggressive-behavior, effects in mammals. U.S. Pat. No. 3,870,706. Other 6-(2-pyridyl) substituted compounds are apparently disclosed in Japanese Kokai 6994/76, Derwent Abstract No. 17551X.

Many of the known compounds have also been disclosed to be useful for increasing the growth rate, productivity and feed-utilization efficiency of meat-producing, milk-producing or egg-laying farm animals. See U.S. Pat. Nos. 3,734,922; 3,767,660; 3,786,149; 3,803,315; 3,821,388; 3,836,660; 3,836,661; 3,840,664; 3,856,802; and 4,000,289.

1-Morpholino-, 1-piperazino-, 1-piperidino-, 1-pyrrolidino-, and 1-(4H-1,4-thiazin-4-yl)-4H-s-triazolo[4,3-a][1,4]benzodiazepines substituted at the 6-position and optionally substituted at the 4- and 8-positions have been disclosed. U.S. Pat. Nos. 3,709,899; 3,767,660; 3,894,025 and 3,996,230; and British Pat. No. 1,323,277.

2,4-Dihydro-1H-s-triazolo[4,3-a][1,4]benzodiazepin-1-thiones substituted with optionally substituted phenyl at the 6-position, optionally substituted at the 4- and 8-positions, and unsubstituted at the 2-position are known. U.S. Pat. Nos. 3,864,356 and 3,865,811.

SUMMARY OF THE INVENTION

The present invention provides (A) A method of treating hypertension in mammals which comprises administering to a mammal suffering from said disease an amount of a compound of formula I
wherein
  (1)-A-(2) is (1)—$CR_1$=N—(2) or (1)—C(=$X_1$)—$NR_{11}$-(2);
wherein
  $R_1$ is
   (a) hydrogen;
   (b) alkyl of 1 to 6 carbon atoms;
   (c) chlorine, bromine or iodine;
   (d) —$CHX_2X_3$ wherein $X_2$ is halogen; and $X_3$, being the same as or different from $X_2$, is hydrogen, methyl, ethyl, fluorine, chlorine, or bromine;
   (e) trifluoromethyl;
   (f) cyano or cyanomethyl;
   (g) —$X_4R_{12}$, wherein $X_4$ is oxygen or sulfur, and $R_{12}$ is alkyl of 1 to 3 carbon atoms or —$(CH_2)_2NR_{15}R_{16}$, wherein $R_{15}$ and $R_{16}$ are the same or different and are hydrogen or methyl;
   (h) —$CH_2X_4R_{13}$, wherein $R_{13}$ is hydrogen or alkyl of 1 to 3 carbon atoms, inclusive;
   (i) 3-pyridyl;
   (j) azetidino, pyrrolidino or piperidino;
   (k) pyrrolidinomethyl;
   (l) 4-methyl-1-piperazinyl; or
   (m) c—$N(CH_2CH_2)_2X_4$;
wherein
  $R_{11}$ is methyl or ethyl; and
wherein
  $X_1$ is oxygen or sulfur;
wherein
  B is —$CHR_4$— or —NH—, wherein $R_4$ is hydrogen or methyl;
wherein
  $R_6$ is
   (a) phenyl;
   (b) phenyl substituted at 1 or 2 positions with halogen, wherein, if disubstituted, the substituents are the same or different; or
   (c) 2-pyridyl; and
wherein
  $R_8$ is hydrogen, halogen, or —$X_8R_{81}$, wherein $X_8$ is sulfur, sulfinyl or sulfonyl and
  $R_{81}$ is alkyl of 1 to 3 carbon atoms; with the provisos that (i) $R_1$ is C—$N(CH_2CH_2)_2X_4$ and $R_6$ is phenyl only when $R_8$ is other than hydrogen;
  (ii) $R_1$ is pyrrolidino only when $R_8$ is other than bromo or iodo;
  (iii) $R_1$ is methyl, B is $CHR_4$ and $R_4$ is hydrogen only when
   (a) $R_8$ is other than —$SR_{81}$, and
   (b) $R_6$ is other than phenyl, o-fluorophenyl, 2,5-difluorophenyl, 2-chloro-5-fluorophenyl, or o-chlorophenyl;
  (iv) $R_1$ is hydrogen, ethyl, n-propyl or isopropyl, and B is —$CHR_4$; or $R_1$ is methyl, B is —$CHR_4$, and $R_4$ is methyl, only when
   (a) $R_8$ is other than —$SR_{81}$, and
   (b) $R_6$ is other than phenyl; and
  (v) $R_1$ is n-butyl, n-pentyl, n-hexyl or isomers thereof only when $R_8$ is other than $SR_{81}$; and
  (vi) B is —NH— only when
   (a) A is —$CR_1$=N—,
   (b) $R_1$ is hydrogen or alkyl of 1 to 6 carbon atoms, and
   (c) $R_6$ is other than 2-pyridyl;
or a pharmacologically acceptable acid addition salt thereof, effective to lower the mammal's systemic arterial blood pressure; and further (B) A compound of formula III
wherein
  (1)-D-(2) is (1)—C(c—$N(CH_2CH_2)_2S$)=N—(2), (1)—C(c—$N(CH_2)_3$)=N—(2), or (1)—C(=S)—$NR_{111}$-(2), wherein $R_{111}$ is methyl or ethyl;
wherein
  $R_{114}$ is hydrogen or methyl;
wherein
  $R_{116}$ is
   (a) phenyl;
   (b) phenyl substituted at 1 or 2 positions with halogen wherein, if disubstituted, the substituents are the same or different; or
   (c) 2-pyridyl; and
wherein $R_{118}$ is hydrogen, halogen or —$X_9R_{91}$, wherein $X_9$ is sulfur, sulfinyl, or sulfonyl and $R_{91}$ is alkyl of 1 to 3 carbon atoms; with the proviso that (1)-D-(1) is (1)—C(c—$N(CH_2CH_2)_2S$)=N—(2) and $R_{116}$ is phenyl only when $R_{118}$ is other than hydrogen; or a pharmacologically acceptable acid addition salt thereof;

(C) A compound of the formula I wherein (1)-A-(2) is (1)—$CR_1$=N—(2);
wherein
  $R_1$ is alkyl of 4 to 6 carbon atoms;
wherein
  B is —NH—;
wherein
  $R_6$ is
   (a) phenyl; and
   (b) phenyl substituted at 1 or 2 positions with halogen,
wherein, if disubstituted, the substituents are the same or different;
wherein $R_8$ is hydrogen or halogen; or a pharmacologically acceptable acid addition salt thereof.

"Alkyl of 1 to 3 carbon atoms" means methyl, ethyl, n-propyl or isopropyl. "Alkyl of 4 to 6 carbon atoms" means n-butyl, n-pentyl, n-hexyl or isomers thereof. "Alkyl of 1 to 6 carbon atoms" means alkyl of 1 to 3 carbon atoms or alkyl of 4 to 6 carbon atoms.

"Halogen" means fluorine, chlorine, bromine or iodine.

Reference herein to a compound of formula I wherein $R_1$ is —$CHX_2X_3$ and wherein $X_2$ differs from $X_3$ includes reference to each of the enantiomers of the compound.

Reference herein to "azetidino," "pyrrolidino," "piperidino," "morpholino," or "thiomorpholino" means that the moiety is linked via a bond from its nitrogen atom to the carbon at position 1 of a 4H-s-triazolo[4,3-a][1,4]benzodiazepine moiety.

The compounds of concern for the present invention are either known or can be prepared as described presently:

A. In all synthetic procedures described below, the starting compound is of formula V, formula VI, or formula X wherein $R_8$ and $R_6$ are as described above for the compound of formula I, $R_{60}$ is any substituent within the scope of $R_6$ except 2-pyridyl, and $R_{10}$ is hydrogen or alkyl of 1 to 3 carbon atoms. All compounds of formulas V, VI and X are known from the disclosures of U.S. Pat. No. 3,422,091, U.S. Pat. No. 3,987,052, and Fryer et al., J. Pharm. Sci. 53, 264 (1964) (for compounds of formula V); U.S. Pat. Nos. 3,709,898 and 3,879,413 and references cited therein (for compound of formula VI); and U.S. Pat. No. 4,082,764, Derieg et al., J. Org. Chem. 36, 782 (1971), and Hester, J. Heterocyclic Chem. 17, 575 (1980) (for compounds of formula X).

B. Using as starting material a compound of formula V, methods to prepare:

(1) the corresponding compounds of formula I wherein (1)-A-(2) is (1)—C(=O)—$NR_{11}$—(2) are known from the disclosure of U.S. Pat. No. 3,646,055; see also Hester, Rudzik and VonVoigtlander, J. Med. Chem. 23,402 (1980).

(2) the corresponding compounds of formula I wherein B is not —NH— and $R_1$ is hydrogen or alkyl of 1 to 3 carbon atoms, inclusive, including the compounds of formula VII, are known from the disclosures of U.S. Pat. Nos. 3,987,052 and 3,734,922; the compounds of formula I wherein (1)-A-(2) is (1)—$CR_1$=N—(2), $R_1$ is alkyl of 4 to 6 carbon atoms, B is —$CHR_4$—, $R_6$ is other than 2-pyridyl, and $R_8$ is hydrogen, halogen, or —$X_8R_{81}$ are known from the disclosure of U.S. Pat. Nos. 3,880,877 and 3,882,101 and can be made by the methods described therein or by methods known in the art, for example by reacting a compound of the formula VIII with an appropriate acid halide.

(3) the corresponding compounds of formula I wherein $R_1$ is 3-pyridyl, —$CH_2SR_{73}$, wherein $R_{73}$ is alkyl or 1 to 3 carbon atoms, pyrrolidinomethyl, and cyanomethyl are known from the disclosures of U.S. Pat. Nos. 3,734,922; 3,856,802; and 3,886,174;

(4) the corresponding compounds of formula I wherein $R_1$ is —$CH_2X_4H$ or —$CH_2OR_{73}$ are known from the disclosure of Hester and VonVoigtlander (1979) cited above and Belgian Pat. No. 782,680. To obtain the compound of formula I wherein $R_1$ is —$CH_2SH$, mercaptoacetic acid hydrazide is reacted with the corresponding compound of formula V.

(5) the corresponding compounds of formula VIII are known from the disclosures of Meguro and Kuwada, Chem. Pharm. Bull. 21, 2375 (1973); U.S. Pat. No. 3,751,426; and Hester, Rudzik and VonVoigtlander, J. Med. Chem. 23, 392 (1980).

C. Using as starting material a compound of formula VI, the method of preparing the corresponding compound of formula IX is known from U.S. Pat. No. 3,709,898. In formula IX, $R_{10}$ is hydrogen or alkyl of one to 3 carbon atoms, inclusive. Using as starting material a compound of formula X, the methods for preparing the corresponding compounds of formula IX are known. Derieg et al., J. Heterocyclic Chem. 8, 181 (1971); Meguro et al., Chem. Pharm. Bull. 21, 1619 (1973); Walser et al., J. Heterocyclic Chem. 12, 717 (1975); Hester, J. Heterocyclic Chem. 17, 575 (1980). Using compounds of formula IX as starting material, methods to prepare all corresponding compounds pertinent to the invention, including those wherein B is —NH— and those of formula VII wherein $R_6$ is not phenyl, are known from U.S. Pat. Nos. 3,709,898; 3,879,413 and 3,891,666.

D. Using as starting material a compound of formula VII, methods to prepare the corresponding compound of formula I wherein $R_1$ is chlorine, bromine, iodine, cyano, —O—$R_{12}$, —$O(CH_2)_2NR_{15}R_{16}$, azetidino, pyrrolidino, piperidino, 4-methyl-1-piperazinyl, morpholino, and thiomorpholino are known from U.S. Pat. Nos. 3,709,899; 3,767,660; 3,894,025; 3,912,753 and 3,996,230. Preparations of the 1-iodo, 1-acetidino and 1-thiomorpholino compounds are illustrated in Examples 1, 2 and 3 below.

E. Using as starting material a compound of formula VIII, methods to prepare:

(1) the corresponding compounds of formula I wherein $R_1$ is trifluoromethyl are known from Hester and VonVoigtlander, cited above;

(2) the corresponding compound of formula I wherein $R_1$ is —$SR_{12}$ or $S(CH_2)_2NR_{15}R_{16}$ are known from Hester and VonVoigtlander, cited above, and U.S. Pat. Nos. 3,751,426 and 3,912,753;

(3) the corresponding compound of formula I wherein $R_1$ is cyanomethyl or —$CHX_2X_3$ are known from U.S. Pat. No. 4,141,902.

An alternative procedure for preparing 8-alkylthio-4H-s-triazolo[4,3-a][1,4]benzodiazepines, except those with halogen at the 1-position, is to first prepare a corresponding 8-halo analog, preferably the bromo or iodo, and then react the 8-halo analog with a corresponding alkali metal mercaptide, $MSR_{81}$, wherein M represents an alkali metal ion, preferably that of sodium, in a solvent such as dimethylformamide, dimethylsulfoxide or the like, preferably dimethylformamide.

A general summary of synthetic procedures for compounds of concern in the present specification is provided by the Hester, Rudzik and Kamdar (1971), Hester and VonVoigtlander (1979), Hester (1980) and two Hester, Rudzik and VonVoigtlander (1980) references cited above, as well as Hester, Chidester and Szmuszkovicz, J. Org. Chem. 44, 2688 (1979).

The preferred method for making compounds of formula II wherein (1)-D-(2) is (1)—C(—C—N($CH_2CH_2$)$_2$S)=N—(2) or (1)—C(C—N($CH_2$)$_3$)-=N—(2), $R_{116}$ is not 2-pyridyl and $R_{118}$ is not alkylthio is to synthesize the corresponding 1-bromo-4H-s-triazolo[4,3-a][1,4]benzodiazepine by bromination with N-bromosuccinimide of the corresponding compound of formula VII, which in turn is synthesized from the corresponding compound of formula X by methods summarized in the Hester (1980) reference cited above. The preferred method for making such compounds of formula III wherein $R_{118}$ is alkylthio is to synthesize the corresponding 8-bromo analog by the preferred method starting from the corresponding compound of formula X wherein $R_8$ is bromine and then use the alternative method provided above for making 8-alkylthio-4H-s-triazolo[4,3-a][1,4]benzodiazepines.

Compounds of formula III wherein (1)-D-(2) is (1)—C(=S)—NR$_{111}$—(2) are synthesized starting with the corresponding thione of formula V. The thione of formula V is reacted in a known process with an alkylhydrazine to yield the compound of formula XI. Hester, Chidester and Szmuszkovicz, J. Org. Chem. 24, 2688 (1979). The resulting compound of formula XI is then reacted with thiophosgene in a suitable solvent in the presence of base to yield the desired compound of formula III. Suitable bases are triethylamine or other organic amine bases, potassium or sodium carbonate, and the like. Suitable solvents are dimethylformamide, N,N-dimethylacetamide, methylene chloride, dioxane, tetrahydrofuran and the like. Preferred is triethylamine as base in tetrahydrofuran as solvent. See Hester and Von-Voigtlander (1979), cited above, wherein the synthesis of the 1-thiol (tautomer of the 1-thione) from the compound of formula VIII by reaction with thiophosgene in the presence of base is described.

Compounds of the formula I wherein (1)-A-(2) is (1)—CR$_1$=N—(2), R$_1$ is alkyl of 4 to 6 carbon atoms, B is CHR$_4$, R$_6$ is 2-pyridyl, and R$_8$ is hydrogen or halogen are prepared: (1) according to the method of U.S. Pat. No. 3,734,922 by reacting an appropriate compound of the formula V with a hydrazide of the formula R$_1$—C(=O)—NH—NH$_2$ wherein R$_1$ is alkyl of 4 to 6 carbon atoms; or alternatively by methods known in the art, for example by reacting an appropriate compound of the formula VIII with an appropriate acid halide.

Compounds of the formula I wherein (1)-A-(2) is (1)—CR$_1$=N—(2), R$_1$ is alkyl of 4 to 6 carbon atoms, B is —NH—, R$_6$ is (a) phenyl or (b) phenyl substituted at 1 or 2 positions with halogen, and R$_8$ is hydrogen or halogen are prepared according to the method of U.S. Pat. No. 3,891,666.

A pharmacologically acceptable acid addition salt of the compounds of formula I or formula III pertinent to the present invention can be made by reacting the free bases of formula I or III with the acid corresponding to the salt to be formed. The pharmacologically acceptable acid addition salts contemplated for the present invention include the hydrochlorides, hydrobromides, hydroiodides, sulfates, nitrates, phosphates, acetates, propionates, palmitates, benzoates, salicylates, hexynoates, phenylbutyrates, naphthoates, glycolates, succinates, nicotinates, tartrates, maleates, malates, pamoates, methanesulphonates, benzynesulfonates, toluenesulfonates, cyclohexanesulfonates, picrates, citrates, lactates, and the like.

Preferred compounds for use in the method of treatment disclosed herein are those of formula I wherein R$_4$ is hydrogen, R$_6$ is phenyl, R$_8$ is chloro, bromo or iodo and R$_1$ is chloro, bromo, iodo, morpholino, thiomorpholino, methylthio or methoxy, or, in the case of the 1-ones or 1-thiones, R$_{11}$ is methyl. More preferred are the preferred compounds wherein R$_8$ is chloro, bromo or iodo and R$_1$ is bromo, iodo or morpholino.

Most preferred are 8-bromo-6-phenyl-1-morpholino-4H-s-triazolo[4,3-a][1,4]benzodiazepine, 1,8-dibromo-6-phenyl-4H-s-triazolo[4,3-a][1,4]benzodiazepine, and 8-bromo-1-chloro-6-phenyl-4H-s-triazolo[4,3-a][1,4]benzodiazepine.

The preferred among the novel 1-thiomorpholino and 1-azetidino compounds of the present invention are those of formula III wherein R$_{114}$ is hydrogen, R$_{116}$ is phenyl and R$_{118}$ is chloro, bromo or iodo. Most preferred are the 8-bromo analogs of the preferred compounds.

The preferred among the novel 1-thione compounds of the present invention are those of formula III wherein R$_{114}$ is hydrogen, R$_{116}$ is phenyl, R$_{118}$ is chloro, bromo or iodo, and R$_{111}$ is methyl. Most preferred is the 8-bromo analog of the preferred compounds.

Preferred among the novel compounds of the formula I of this invention wherein (1)-A-(2) is (1)—CR$_1$=N—(2), and R$_1$ is alkyl of 4 to 6 carbon atoms are those wherein R$_1$ is n-butyl and R$_8$ is halogen. Most preferred is the 8-bromo analog of the preferred compounds.

The method which comprises the present invention is to treat hypertension in mammals suffering therefrom. The invention is preferably applied to humans.

The skilled physician is able to ascertain by standard techniques when a human is suffering from hypertension, a disease characterized by a pathologically elevated, systemic arterial blood pressure. Hypertension in a human is indicated by a diastolic blood pressure (sitting) above about 85 mm Hg and a systolic blood pressure (sitting) above about 120 mm Hg. Diastolic blood pressure (sitting) above about 95 mm Hg and systolic blood pressure (sitting) above about 140 mm Hg are especially indicative of hypertension in a human.

The skilled veterinarian can ascertain when a non-human mammal is suffering from hypertension, i.e. pathologically elevated, systemic arterial blood pressure.

It is contemplated that, in carrying out the present invention, the compounds to which it pertains will be administered by any suitable route, including oral, parenteral, rectal, vaginal or transdermal. Accordingly, the pharmaceutical forms contemplated for carrying out the invention include pharmaceutical forms appropriate to these routes of administration, including tablets, capsules, powders and powder packets, cachets, dragees, solutions, suspensions, sterile injectable forms, suppositories, bougies, suspensions in membranes on tampons or other support means, and the like. In preparing these forms, the active compounds may be combined with suitable, pharmaceutically acceptable diluents or carriers such as carbohydrates (e.g., lactose or sucrose), proteins, lipids, calcium phosphate, cornstarch, stearic acid, methylcellulose, various oils (e.g., coconut, sesame, safflower, cottonseed, peanut or corn), water or aqueous solutions, or various polymeric membranes (e.g., polyvinylacetate films). Sweetening, coloring and flavoring agents may be added to the various formulations or used to coat the pharmaceutical forms.

The preferred route of administration is oral.

The method of treatment disclosed herein may be applied alone to treat a mammal suffering from hypertension or may be employed concomitantly or in conjunction with other methods for treating a mammal suffering from the disease, such as administration of other antihypertensive agents, dietary restrictions, and the like.

The dosage regimen for treating a mammal suffering from hypertension by the method of the present invention is determined in accordance with a variety of factors including the species, age, weight, sex, medical condition and severity of the hypertension of the mammal being treated, the particular compound or compounds being employed, the route of administration of such compound or compounds, and whether other methods for treating the mammal for hypertension are also employed. A skilled physician or veterinarian will readily ascertain and prescribe the correct amount of compound to be administered in carrying out the method of the present invention. In so doing, the physician or veternarian could employ relatively low dosages at first and subsequently increase dosages until the desired reduction in blood pressure is obtained.

For oral administration to a human, daily doses can vary from about 0.1 to about 1000 mg per day of active compound in carrying out the method of the present invention. An equivalent dosage range for administration by other suitable routes may also be employed.

EXAMPLE 1

8-Chloro-6-phenyl-1-thiomorpholino-4H-s-triazolo[4,3-a][1,4]benzodiazepine

A mixture of 2.0 gm (5.35 mmol) of 8-chloro-1-bromo-6-phenyl-4H-s-triazolo[4,3-a][1,4]benzodiazepine and 2.0 ml of thiomorpholine was heated under nitrogen in an oil bath at 120° C. for 18 hr and then allowed to cool. The reaction mixture was treated with methylene chloride and water. The organic layer was separated, washed with dilute brine and concentrated in vacuo. The residue was recrystallized from methanol to yield 1.40 gm (72.7%) with m.p. 241°–243° C. and 0.46 gm (23.9%) with m.p. 239°–241° C. of the title product. Analysis of the title product for carbon, hydrogen, nitrogen, chlorine and sulphur revealed 60.47% C, 4.58% H, 18.03% N, 9.14% Cl, and 8.09% S. Calculated values for such an analysis for the title product are: 60.67% C, 4.58% H, 17.69% N, 8.98% Cl, and 8.10% S.

Following the procedure of Example 1 but using as starting material, instead of the 8-chloro-1-bromo-6-phenyl-4H-s-triazolo[4,3-a][1,4]benzodiazepine, the 1,8-dibromo or 1-bromo-8-iodo analogs thereof, 8-bromo-6-phenyl-1-thiomorpholino-4H-s-triazolo[4,3-a][1,4]benzodiazepine or 8-iodo-6-phenyl-1-thiomorpholino-4H-s-triazolo[4,3-a][1,4]benzodiazepine are obtained.

EXAMPLE 2

8-Bromo-1-iodo-6-phenyl-4H-s-triazolo[4,3-a][1,4]benzodiazepine

A stirred mixture of 0.339 gm (1 mmol) of 8-bromo-6-phenyl-4H-s-triazolo[4,3-a][1,4]benzodiazepine and 25 ml of benzene was treated with 0.242 gm (1.1 mmol) of N-iodosuccinimide and refluxed under nitrogen for 12 hr and 40 min. The mixture was cooled and was then mixed with ice water containing sodium bicarbonate and sodium chloride and was finally extracted with methylene chloride. The extract was washed with dilute sodium chloride, dried with sodium sulfate and concentrated in vacuo. The residue was crystallized from methylene chloride-methanol to yield one batch of 0.252 gm, which melted with decomposition between 209° and 212.5° C. and another batch of 0.020 gm which melted with decomposition between 196° and 198.5° C. A portion of the first batch was recrystallized twice by being dissolved in almost pure methylene chloride to which methanol was slowly added during concentration. After this recrystallization, the title product melted with decomposition between 200° and 207° C. Another sample for analysis was prepared by essentially the same procedure and, after recrystallization from methylene chloride-methanol, molded with decomposition between 216° and 219° C. Analysis of the product for carbon, hydrogen and nitrogen showed C: 41.04%, H: 2.11%, N: 12.10%. Calculated values for such an analysis of the product are: C: 41.31%; H: 2.16% and N: 12.05%.

EXAMPLE 3

8-chloro-6-phenyl-1-azetidino-4H-s-triazolo[4,3-a][1,4]benzodiazepine 0.20 gm of 1-bromo-8-chloro-6-phenyl-4H-s-triazolo[4,3-a][1,4]benzodiazepine was mixed with 1.0 ml of trimethyleneimine and 0.09 gm of potassium carbonate. The mixture was heated under N₂ at 75° C. for 3.5 hours and then allowed to cool to room temperature. The mixture was then poured into ice water. A solid precipitated, was collected on a filter, washed twice with water, and dried in vacuo. The solid was then recrystallized from ethylacetate to yield 0.12 gm of title product, m.p. 198°–200° C.

Following the procedure of example 3 but using as starting material, instead of the 1-bromo-8-chloro-6-phenyl-4H-s-triazolo[4,3-a][1,4]benzodiazepine, the 1,8-dibromo or 1-bromo-8-iodo analogs thereof, 8-bromo-6-phenyl-1-azetidino-4H-s-triazolo[4,3-a][1,4]benzodiazepine or 8-iodo-6-phenyl-1-azetidino-4H-s-triazolo[4,3-a][1,4]benzodiazepine are obtained.

EXAMPLE 4

8-Bromo-1-propyl-6-(2-pyridinyl)-4H-[1,2,4]triazolo[4,3-a][1,4]benzodiazepine.

A mixture of 1.5 g of 7-bromo-2-hydrazino-5-(2-pyridinyl)-3H-1,4-benzodiazepine in 45 ml of tetrahydrofuran cooled in an ice bath over a nitrogen atmosphere is added 0.57 ml of butyryl chloride dropwise over 90 sec. After stirring for 4.5 hrs, there is added an additional 0.1 ml of butyryl chloride. The resulting mixture is then stirred at ambient temperature for 18 hrs, poured into 300 ml of aqueous sodium bicarbonate and filtered. The filtrate is extracted with dichloromethane, washed with dilute brine, dried over sodium sulphate, and concentrated under reduced pressure. The resulting residue is then heated in an oil bath at 120°–125° C. for 45 min, allowed to cool, and concentrated under reduced pressure. The residue is then dissolved in dichloromethane, washed with aqueous sodium bicarbonate and dilute brine, dried over sodium sulphate, and concentrated under reduced pressure. The resulting residue is then chromatographed on 150 g of silica gel eluting with 2.5% methanol in dichloromethane. Crystallization from ethyl acetate yields 0.27 g of title product. Melting point is 184°–186° C.

EXAMPLE 5

8-Bromo-1-butyl-6-phenyl-4H-[1,2,4]triazolo[4,3-a][1,4]benzodiazepine.

To a solution of 2 g of 7-bromo-2-hydrazino-5-phenyl-3H-[1,4]benzodiazepine in 60 ml of tetrahydrofuran cooled in an ice bath under a nitrogen atmosphere is added 0.87 ml of valeryl chloride dropwise over 3 min. After stirring for 2.5 hrs, the reaction mixture is then poured into 100 ml of water and aqueous sodium bicarbonate. A solid precipitate is then collected on a filter, washed with water and dried. The resulting residue is then dissolved in 25 ml of acetic acid, heated under a nitrogen atmosphere in an oil bath to 125° C. for 35 min, allowed to cool, and concentrated under reduced pressure. Crystallization of the residue from a mixture of methanol and water yields 0.88 g of title product with melting point 87°–90° C. and 0.41 g of title product with melting point 88°–90° C. as a monohydrate.

EXAMPLE 6

8-Bromo-1-(2,2-dimethylpropyl)-6-phenyl-4H-[1,2,4]triazolo[4,3-a][1,4]benzodiazepine.

Following the procedure of Example 5, 2.0 g of 7-bromo-2-hydrazino-5-phenyl-3H-1,4-benzodiazepine is reacted with 1.01 ml of tert-butyl acetylchloride to yield 1.17 g of title product with melting point 229.5°–232° C. and 0.30 g of title product with melting point 205°–219° C.

EXAMPLE 7

8-Bromo-1-(2-methylpropyl)-6-phenyl-4H-[1,2,4]triazolo[4,3-a][1,4]benzodiazepine.

Following the procedure of Example 5, 2.5 g of 7-bromo-2-hydrazino-5-phenyl-3H-1,4-benzodiazepine and 1.11 ml of isovaleryl chloride is transformed to 1.03 g of title product with melting point 93°–95° C.

EXAMPLE 8

The hypotensive activity of compounds pertinent to the present invention was determined by tests on rats and baroreceptor-denervated cats:

A. Tests on Rats

Female Sprague-Dawley rats weighing 200–250 gm were fasted for 22–28 hours prior to anesthesia by intravenous (tail vein) administration of 8 ml/kg of a 5% glucose solution containing 5 mg/ml of α-chloralose, 5 mg/ml of urethane and 1.87 mg/ml of sodium pentobarbital.

Thirty minutes after anesthesia, the right external jugular vein and left common carotid artery were cannulated with PE-50 catheters, which had been pre-filled with 0.2 ml of 20 units/ml of heparanized saline.

Arterial pressures were continuously recorded through the arterial cannula with a Statham P23Gc transducer and Grass Model 7 polygraph.

All substances administered intravenously were administered through the venous cannula. Every intravenous administration of test compound of vehicle (N,N-dimethylacetamide) was followed by a rinse with 0.2 ml of 20 units/ml of heparanized saline.

The rats were affixed prone to test tube racks, one rat per rack, with 0 silk ligatures in their loose axillary skin. The racks were variably heated by passing warm water, at variable temperature and flow rate, through vinyl tubing passing through the racks. The rats were covered with aluminum foil domes and the heating was varied to maintain the rats' rectal temperatures between 34° and 37° C.

Sometime after the rats had been affixed to the racks and 90 minutes after administration of anesthetic, a 20 minute pre-treatment period was begun. During this period, the rats' arterial pressures stabilized to base-line values.

Following the 20 minute pre-treatment period, rats were dosed intravenously with vehicle alone (0.19 ml/kg of N,N-dimethylacetamide) as control or a test compound in vehicle. Vehicle control or test compound (dissolved in N,N-dimethylacetamide so that, to achieve the desired dose, 0.19 ml/kg of solution had to be administered) was administered cumulatively according to the following schedule:

| TIME (Post-treatment) min. | DOSE Vehicle Alone (control) ml/kg | Test Compound (in 0.19 ml of solution in vehicle) mg/kg |
|---|---|---|
| 0 | 0.19 | 0.03 |
| 20 | 0.19 | 0.3 |
| 40 | 0.19 | 3.0 |

For vehicle alone and each test compound, the procedure was applied to a group of at least four rats. For each such group, all rats were subjected to the procedure together, but the procedures started on individual rats 5–7 minutes apart.

For each rat, arterial pressures at 0 minute (just before first administration of vehicle or test compound), 20 minutes post-treatment (just before second administration of vehicle or test compound), 40 minutes post-treatment (just before third administration of vehicle or test compound), and 60 minutes post-treatment were determined. Thus, for each rat, the differences in arterial pressure at 20, 40, or 60 minutes post-treatment from that at 0 minutes could be determined. For each test compound and the vehicle alone as control, the average of each of these differences for all rats in the test or control group was determined. It is these averages, mean arterial pressure (MAP) changes, which were taken as the measure of the blood pressure-lowering effect of test compound (in vehicle) or vehicle alone and which are entered under "MAP Change" in Table A below.

Essentially the same procedure was applied with minoxidil (2,4-diamino-6-piperidinopyrimidine-3-oxide), a compound known to be an antihypertensive agent in humans. At post-treatment time 0, 3 to 5 mg/kg of minoxidil in 0.1M citric acid as vehicle (1.0 ml/kg dose volume) was administered to the rats. At 15 minutes post-treatment, the arterial blood pressure of the rats was reduced 16±2 mm Hg, and at 30 minutes post-treatment their arterial blood pressure was reduced 19±3 mm Hg. In control rats, at post-treatment time 0 administered 1 ml/kg of 0.1M citric acid, arterial blood pressure was reduced 4±1 mm Hg at 15 minutes and 6±1 mm Hg at 30 minutes post-treatment.

The procedure was also applied with clonidine (2-(2,6-dichloroanilino)-2-imidazoline), also a compound known to be an hypotensive agent in humans. At post-treatment time 0, 0.015 mg/kg of clonidine was administered in 0.9% sodium chloride as vehicle (0.5 ml/kg dose volume). At 15 minutes post-treatment, the arterial blood pressure of the rats was reduced 24±6 mm Hg, and at 30 minutes post-treatment their blood pressures were reduced 28±5 mm Hg. The aqueous sodium chloride vehicle alone was found to have no effect on the rats' blood pressure.

TABLE A

| Compound of Formula I B is —CH$_2$—, A is —CR$_1$=N— | | | MAP change (mm/Hg) at | | |
|---|---|---|---|---|---|
| | | | | plus 0.03 | plus 0.3 | plus 3.0 |
| R$_1$ | R$_6$ | R$_8$ | 0.03 mg/kg | 0.3 mg/kg | 3.0 mg/kg |
| morpholino | phenyl | Cl | −10 | −13 | −22 |
| morpholino | phenyl | Br | −7 | −14 | −23 |
| morpholino | o-chlorophenyl | Cl | −6 | −17 | −19 |
| H | 2-pyridyl | Br | −1 | −14 | −22 |

TABLE A-continued

| Compound of Formula I | | | MAP change (mm/Hg) at | | |
|---|---|---|---|---|---|
| $CH_3S$ | phenyl | Br | −6 | −14 | −26 |
| I | phenyl | Br | −2 | −11 | −20 |
| Br | phenyl | Cl | −8 | −18 | −28 |
| Br | phenyl | Br | −9 | −18 | −28 |
| Cl | phenyl | Br[1] | −12 | −17 | −26 |
| pyrrolidino | phenyl | Cl | −6 | −14 | −27 |
| 3-pyridyl | phenyl | Cl | −9 | −13 | −26 |
| thiomorpholino | phenyl | Cl | −5 | −6 | −18 |
| morpholino | phenyl | —$SCH_3$[1] | −3 | −6 | −17 |
| B is —$CH_2$—, A is —C(=O)—$NR_{11}$—: | | | | | |
| $R_{11}$ | $R_6$ | $R_8$ | | | |
| $CH_3$ | phenyl | Cl | −6 | −11 | −21 |
| B is —NH—: | | | | | |
| $R_1$ | $R_6$ | $R_8$ | | | |
| $CH_3$ | phenyl | Cl | −4 plus 0.19 ml/kg | −9 plus 0.19 ml/kg | −16 plus 0.19 ml/kg |
| Control (N,N—dimethylacetamide) | | | −5 | −6 | −7 |

[1]Compound tested on 3 rats

B. Tests on Baroreceptor-denervated Cats

Compounds were tested for hypotensive activity in the baroreceptor-denervated cat. See, e.g., McCall et al., Europ. J. Pharmacol. 36, 69 (1976); McCall et al., J. Auton. Nerv. Sys. 3, 9 (1981).

Except as noted herein, the details of the procedure used are provided in the McCall et al. 1981 reference cited above.

Cats were anesthetized by i.p. injection of a mixture of diallyl barbiturate (60 mg/kg), urethane (240 mg/kg) and monoethylurea (240 mg/kg). The cats were then placed in a stereotaxic apparatus and were artificially respired with a Harvard respirator (50 cc×12 cpm). Arterial pressure was measured directly from a femoral artery cannula with a Statham transducer and a Grass polygraph. The cats were baroreceptor denervated by bilaterally sectioning the carotid sinus nerves, the vagi, and the aortic depressor nerves after everting the trachea and esophagus into the mouth. The external carotid nerve was isolated at its juncture with the superior cervical ganglion for monophasic recording of sympathetic discharges under oil with a platinum electrode. Acceptable nerve activity was not considered a prerequisite for inclusion into the study.

The cats were allowed to stabilize for a minimum of one hour following baroreceptor-denervation. After a 5–10 minute pre-treatment period, the cats were dosed intravenously with 0.03 mg/kg of a test compound. Subsequent to this initial dose, the drug was supplemented in a progressive, incremental fashion to total intravenous doses of 0.1, 0.3, 1.0, and 3.0 mg/kg at 30 minute intervals. The drug concentration for the first two dosages (0.03 mg/kg and 0.07 mg/kg) was 3.0 mg/ml in vehicle (N,N-dimethylacetamide). The drug concentration for the last three dosages (0.2 mg/kg, 0.7 mg/kg and 2.0 mg/kg) was 30.0 mg/ml in vehicle. Similarly prepared, untreated control cats received the vehicle alone in the following dosages: 0.01 ml/kg at post-treatment time 0, 0.023 ml/kg at post-treatment time 30 minutes, 0.007 ml/kg at post-treatment time one hour, 0.023 ml/kg at post-treatment time 1.5 hour, and 0.067 ml/kg at post-treatment time 2 hours.

Arterial pressure and integrated sympathetic nerve activity (SNA) were determined at 30 minutes after each administration of test compound or vehicle alone, just before a subsequent administration, if any, of test compound or vehicle.

Each mean arterial pressure change (MAP Change) reported in Table B is the average, for all cats in the group involved, of the differences between the arterial pressure at the time of measurement and that at post-treatment time 0. Similarly, each SNA reported in the Table is the average, for all cats in the group involved, of the percentage of activity at the time of measurement relative to that at post-treatment time 0.

TABLE B

| Compound of Formula I | | | | | Dose (Cumulative) | MAP Change mm Hg | SNA (Relative to post-treatment time O, mean) % |
|---|---|---|---|---|---|---|---|
| $R_1$ | $R_4$ | $R_6$ | $R_8$ | $N^1$ | mg/kg | | |
| morpholino | H | phenyl | Cl | 4 | 0.03 | −29 | −34 |
| | | | | | 0.1 | −26 | −50 |
| | | | | | 0.3 | −34 | −56 |
| | | | | | 1.0 | −47 | −63 |
| | | | | | 3.0 | −51 | −73 |
| morpholino | $CH_3$ | phenyl | Cl | 5 | 0.03 | ND | ND |
| | | | | | 0.1 | ND | ND |
| | | | | | 0.3 | −11 | −34 |
| | | | | | 1.0 | −27 | −60 |
| | | | | | 3.0 | −48 | −35 |
| morpholino | H | o-chlorophenyl | Cl | 2 | 0.03 | +2 | −35 |
| | | | | | 0.1 | −28 | −54 |
| | | | | | 0.3 | −29 | −35 |
| | | | | | 1.0 | −34 | −49 |
| | | | | | 3.0 | −29 | −53 |
| morpholino | H | phenyl | Br | 7 | 0.03 | −4 | −4 |
| | | | | | 0.1 | −17 | −32 |
| | | | | | 0.3 | −23 | −53 |
| | | | | | 1.0 | −41 | −72 |
| | | | | | 3.0 | −42 | −75 |
| 8-chloro-1-methyl-4H—s-triazolo[4,3-a][1,3,4]-benzotriazepine | | | | 2 | 0.03 | −3 | ND |
| | | | | | 0.1 | −5 | ND |
| | | | | | 0.3 | −7 | −40 |
| | | | | | 1.0 | −14 | ND |
| | | | | | 3.0 | −15 | −24 |
| | | | | | ml/kg | | |
| Vehicle (N,N—dimethyl acetamide) | | | | 7 | 0.01 | +6 | 0 |
| | | | | | 0.033 | +6 | +15 |

TABLE B-continued

| Compound of Formula I | | | | Dose | MAP Change | SNA (Relative to post-treatment |
|---|---|---|---|---|---|---|
| $R_1$ | $R_4$ | $R_6$ | $R_8$ $N^1$ | (Cumulative) | mm Hg | time O, mean) % |
| | | | | 0.04 | +6 | +24 |
| | | | | 0.063 | +4 | +35 |
| | | | | 0.13 | +3 | +34 |

[1] Number of cats used in test of compound
ND = not determined

FORMULAS

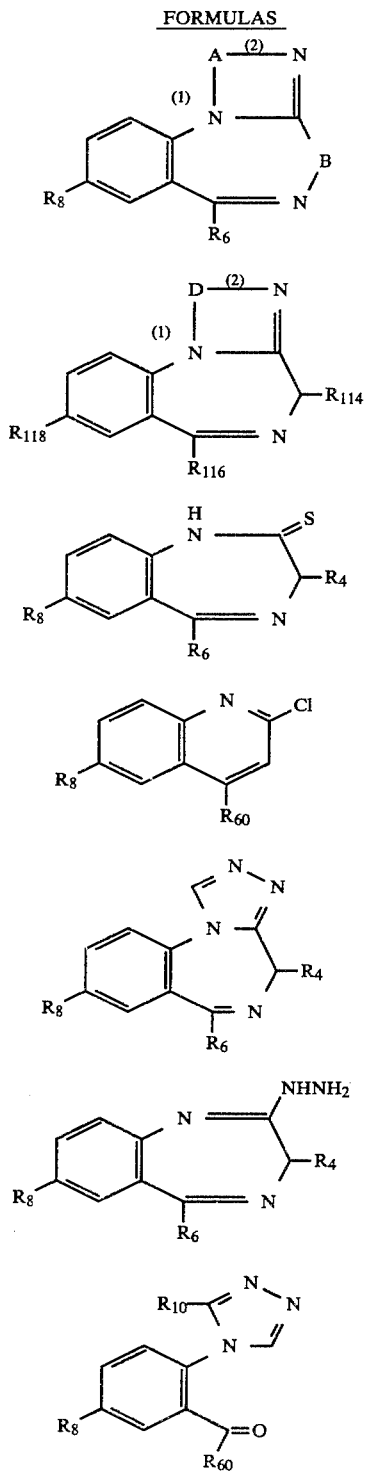

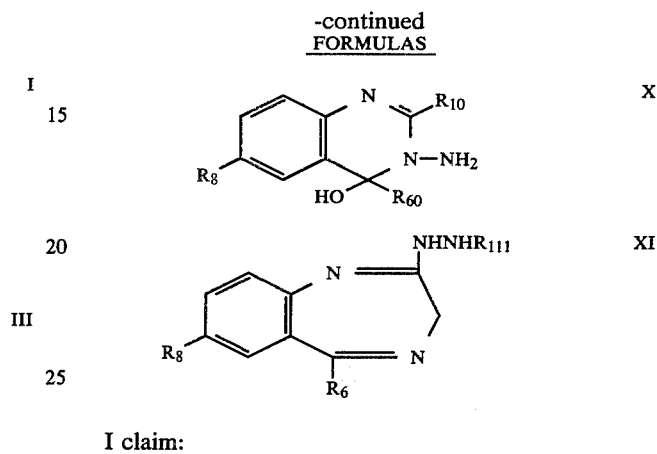

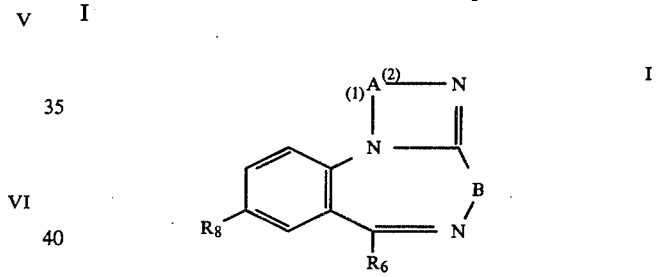

I claim:
1. A method of treating hypertension in mammals which comprises administering to a mammal suffering from said disease an amount of a compound of formula I wherein
(1)-A-(2) is (1)—$CR_1$=N—(2) or (1)—C(=$X_1$)—$NR_{11}$—(2);
wherein
$R_1$ is
 (a) hydrogen;
 (b) alkyl of 1 to 6 carbon atoms;
 (c) chlorine, bromine or iodine;
 (d) —$CHX_2X_3$ wherein $X_2$ is halogen; and $X_3$, being the same as or different from $X_2$, is hydrogen, methyl, ethyl, fluorine, chlorine, or bromine;
 (e) trifluoromethyl;
 (f) cyano or cyanomethyl;
 (g) —$X_4R_{12}$, wherein $X_4$ is oxygen or sulfur, and $R_{12}$ is alkyl of 1 to 3 carbon atoms or —$(CH_2)_2NR_{15}R_{16}$, wherein $R_{15}$ and $R_{16}$ are the same or different and are hydrogen or methyl;
 (h) —$CH_2X_4R_{13}$, wherein $R_{13}$ is hydrogen or alkyl of 1 to 3 carbon atoms, inclusive;
 (i) 3-pyridyl;
 (j) azetidino, pyrrolidino or piperidino;
 (k) pyrrolidinomethyl;
 (l) 4-methyl-1-piperazinyl; or
 (m) c—$N(CH_2CH_2)_2X_4$;
wherein $R_{11}$ is methyl or ethyl; and
wherein
$X_1$ is oxygen or sulfur;
wherein
B is —$CHR_4$— or —NH—, wherein $R_4$ is hydrogen or methyl;
wherein
$R_6$ is
(a) phenyl;
(b) phenyl substituted at 1 or 2 positions with halogen, wherein, if disubstituted, the substituents are the same or different; or
(c) 2-pyridyl; and
wherein
$R_8$ is hydrogen, halogen, or —$X_8R_{81}$, wherein $X_8$ is sulfur, sulfinyl or sulfonyl and $R_{81}$ is alkyl of 1 to 3 carbon atoms; with the provisos that
(i) $R_1$ is c—$N(CH_2CH_2)_2X_4$ and $R_6$ is phenyl only when $R_8$ is other than hydrogen;
(ii) $R_1$ is pyrrolidino only when $R_8$ is other than bromo or iodo;
(iii) $R_1$ is methyl, B is $CHR_4$ and $R_4$ is hydrogen only when
  (a) $R_8$ is other than —$SR_{81}$, and
  (b) $R_6$ is other than phenyl, o-fluorophenyl, 2,5-difluorophenyl, 2-chloro-5-fluorophenyl, or o-chlorophenyl;
(iv) $R_1$ is hydrogen, ethyl, n-propyl or isopropyl, and B is —$CHR_4$; or $R_1$ is methyl, B is —$CHR_4$, and $R_4$ is methyl, only when
  (a) $R_8$ is other than —$SR_{81}$, and
  (b) $R_6$ is other than phenyl; and
(v) $R_1$ is n-butyl, n-pentyl, n-hexyl or isomers thereof only when $R_8$ is other than $SR_{81}$; and
(vi) B is —NH— only when
  (a) A is —$CR_1=N$—,
  (b) $R_1$ is hydrogen or alkyl of 1 to 6 carbon atoms, and
  (c) $R_6$ is other than 2-pyridyl;
or a pharmacologically acceptable acid addition salt thereof, effective to lower the mammal's systemic arterial blood pressure.

2. A method according to claim 1 wherein the compound is one in which A is —$CR_1=N$—; B is —$CHR_4$—; $R_4$ is hydrogen; $R_1$ is methyl, ethyl, n-propyl, chlorine, bromine, iodine, methoxy, ethoxy, methylthio, ethylthio, n-propylthio, 3-pyridyl, morpholino or thiomorpholino; $R_8$ is hydrogen or halogen; and $R_6$ is phenyl, o-chlorophenyl, p-chlorophenyl or 2-pyridyl, with the provisos that $R_1$ is methyl only when $R_6$ is other than phenyl or o-chlorophenyl and $R_1$ is ethyl or n-propyl only when $R_6$ is other than phenyl.

3. A method according to claim 1 wherein the compound is one in which B is —NH—; $R_1$ is methyl; $R_8$ is chlorine, bromine or iodine; and $R_6$ is phenyl, o-chlorophenyl or p-chlorophenyl.

4. A method according to claim 1 wherein the compound is one in which A is —$C(=X_1)$—$NR_{11}$—; $R_{11}$ is methyl or ethyl; $R_8$ is hydrogen or halogen; and $R_6$ is phenyl, o-chlorophenyl, p-chlorophenyl or 2-pyridyl.

5. A method according to claim 2 wherein the compound is one of the group comprising the 4H-s-triazolo[4,3-a][1,4]benzodiazepines of formula II

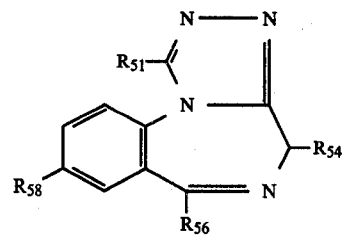

defined as follows, or a pharmacologically acceptable acid addition salt thereof:

| | $R_{51}$ | $R_{54}$ | $R_{56}$ | $R_{58}$ |
|---|---|---|---|---|
| (1) | Cl | H | phenyl | Cl |
| (2) | Cl | H | phenyl | Br |
| (3) | Cl | H | phenyl | I |
| (4) | Br | H | phenyl | Cl |
| (5) | Br | H | phenyl | Br |
| (6) | Br | H | phenyl | I |
| (7) | I | H | phenyl | Br |
| (8) | morpholino | H | phenyl | Cl |
| (9) | morpholino | $CH_3$ | phenyl | Cl |
| (10) | morpholino | H | phenyl | Br |
| (11) | morpholino | H | o-chlorophenyl | H |
| (12) | morpholino | H | o-chlorophenyl | Cl |
| (13) | morpholino | H | phenyl | —$SCH_3$ |
| (14) | morpholino | H | 2-pyridyl | Br |
| (15) | morpholino | H | phenyl | I |
| (16) | morpholino | H | o-chlorophenyl | I |
| (17) | morpholino | H | p-chlorophenyl | Cl |
| (18) | thiomorpholino | H | phenyl | Cl |
| (19) | thiomorpholino | H | phenyl | Br |
| (20) | H | H | 2-pyridyl | Br |
| (21) | $CH_3$ | H | o-chlorophenyl | H |
| (22) | $CH_3$ | H | p-chlorophenyl | Br |
| (23) | $CH_3$ | H | 2-pyridyl | Cl |
| (24) | n-$C_3H_7$ | H | 2-pyridyl | Br |
| (25) | 3-pyridyl | H | phenyl | Cl |
| (26) | azetidino | H | phenyl | Cl |
| (27) | azetidino | H | phenyl | Br |
| (28) | pyrrolidino | H | phenyl | Cl |
| (29) | piperidino | H | phenyl | Br |
| (30) | 4-methyl-1-piperazinyl | H | phenyl | Cl |
| (31) | 4-methyl-1-piperazinyl | H | 2-pyridyl | Br |
| (32) | pyrrolidinomethyl | H | phenyl | Cl |
| (33) | $CF_3$ | H | phenyl | Cl |
| (34) | $CH_3S$ | H | phenyl | Br |
| (35) | $CH_3S$ | H | phenyl | Cl |
| (36) | $C_2H_5S$ | H | phenyl | Br |
| (37) | $C_2H_5S$ | H | phenyl | Cl |
| (38) | $CH_3O$ | H | phenyl | Br |
| (39) | $CH_3O$ | H | phenyl | Cl |
| (40) | $HOCH_2$ | H | phenyl | Cl |
| (41) | $CH_3OCH_2$ | H | phenyl | Cl |
| (42) | $(CH_3)_2N(CH_2)_2S$ | H | phenyl | Cl |

6. A method according to claim 3 wherein the compound is one of the group comprising
8-chloro-1-methyl-6-phenyl-4H-s-triazolo1[4,3-a][1,3,4]benzotriazepine,
8-bromo-1-methyl-6-phenyl-4H-s-triazolo[4,3-a][1,3,4]benzotriazepine, and
8-iodo-1-methyl-6-phenyl-4H-s-triazolo[4,3-a][1,3,4]benzotriazepine,
or a pharmacologically acceptable acid addition salt thereof.

7. A method according to claim 4 wherein the compound is one in which $X_1$ is oxygen.

8. A method according to claim 4 wherein the compound is one in which $X_1$ is sulfur.

9. A method according to claim 7 wherein the compound is one of the group comprising
    8-chloro-2,4-dihydro-2-methyl-6-phenyl-1H-s-triazolo[4,3-a][1,4]benzodiazepin-1-one,
    8-bromo-2,4-dihydro-2-methyl-6-phenyl-1H-s-triazolo[4,3-a]-[1,4]benzodiazepin-1-one,
    8-iodo-2,4-dihydro-2-methyl-6-phenyl-1H-s-triazolo[4,3-a]-[1,4]benzodiazepin-1-one,
    8-chloro-2,4-dihydro-2-ethyl-6-phenyl-1H-s-triazolo[4,3-a]-[1,4]benzodiazepin-1-one,
    8-bromo-2,4-dihydro-2-ethyl-6-phenyl-1H-s-triazolo[4,3-a]-[1,4]benzodiazepin-1-one, and
    8-iodo-2,4-dihydro-2-ethyl-6-phenyl-1H-s-triazolo[4,3-a]-[1,4]benzodiazepin-1-one,
or a pharmacologically acceptable acid addition salt thereof.

10. A method according to claim 8 wherein the compound is one of the group comprising
    8-chloro-2,4-dihydro-2-methyl-6-phenyl-1H-s-triazolo[4,3-a]-[1,4]benzodiazepin-1-thione,
    8-bromo-2,4-dihydro-2-methyl-6-phenyl-1H-s-triazolo[4,3-a]-[1,4]benzodiazepin-1-thione,
    8-iodo-2,4-dihydro-2-methyl-6-phenyl-1H-s-triazolo[4,3-a]-[1,4]benzodiazepin-1-thione,
    8-chloro-2,4-dihydro-2-ethyl-6-phenyl-1H-s-triazolo[4,3-a]-[1,4]benzodiazepin-1-thione,
    8-bromo-2,4-dihydro-2-ethyl-6-phenyl-1H-s-triazolo[4,3-a]-[1,4]benzodiazepin-1-thione, and
    8-iodo-2,4-dihydro-2-ethyl-6-phenyl-1H-s-triazolo[4,3-a]-[1,4]benzodiazepin-1-thione,
or a pharmacologically acceptable acid addition salt thereof.

11. A compound of formula III

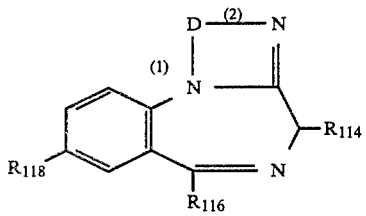

wherein
(1)-D-(2) is (1)—C(c—N(CH$_2$CH$_2$)$_2$S)=N—(2), or
(1)—C(c—N(CH$_2$)$_3$)=N—(2),
wherein
$R_{14}$ is hydrogen or methyl;
wherein
$R_{116}$ is
  (a) phenyl;
  (b) phenyl substituted at 1 or 2 positions with halogen wherein, if disubstituted, the substituents are the same or different; or
  (c) 2-pyridyl; and
wherein
$R_{118}$ is hydrogen, halogen or —X$_9$R$_{91}$, wherein X$_9$ is sulfur, sulfinyl, or sulfonyl and R$_{91}$ is alkyl of 1 to 3 carbon atoms; with the proviso that (1)-D-(2) is (1)—C(c—N(CH$_2$CH$_2$)$_2$S)=N—(2) and $R_{116}$ is phenyl only when $R_{118}$ is other than hydrogen;
or a pharmacologically acceptable acid addition salt thereof.

12. A compound according to claim 11 wherein (1)-D-(2) is (1)—C(c—N(CH$_2$CH$_2$)$_2$S)=N—(2), $R_{114}$ is hydrogen, $R_{116}$ is phenyl, o-chlorophenyl, p-chlorophenyl or 2-pyridyl, and $R_{118}$ is hydrogen or halogen, with the proviso that, when $R_{116}$ is phenyl, $R_{118}$ is other than hydrogen.

13. A compound according to claim 11 wherein (1)-D-(2) is (1)—C(c—N(CH$_2$)$_3$)=N—(2), $R_{114}$ is hydrogen, $R_{116}$ is phenyl, o-chlorophenyl, p-chlorophenyl or 2-pyridyl, and $R_{118}$ is hydrogen or halogen.

14. A compound according to claim 12 selected from the group comprising the 1-thiomorpholino-4H-s-triazolo[4,3-a][1,4]-benzodiazepines of formula XVI

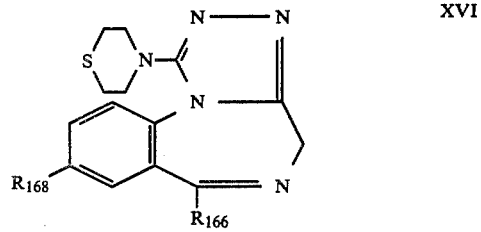

defined as follows, or a pharmacologically acceptable acid addition salt thereof:

| | $R_{166}$ | $R_{168}$ |
|---|---|---|
| (1) | phenyl | Cl |
| (2) | phenyl | Br |
| (3) | phenyl | I |
| (4) | o-chlorophenyl | Cl |
| (5) | o-chlorophenyl | Br |
| (6) | o-chlorophenyl | I |
| (7) | 2-pyridyl | Cl |
| (8) | 2-pyridyl | Br |
| (9) | 2-pyridyl | I |

15. A compound according to claim 13 selected from the group comprising the 1-azetidino-4H-s-triazolo[4,3-a][1,4]benzodiazepines of formula XVII

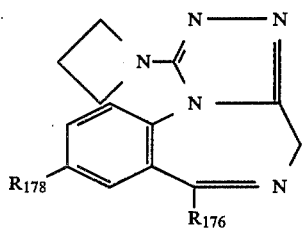

defined as follows, or a pharmacologically acceptable acid addition salt thereof:

| | $R_{176}$ | $R_{178}$ |
|---|---|---|
| (1) | phenyl | Cl |
| (2) | phenyl | Br |
| (3) | phenyl | I |
| (4) | o-chlorophenyl | Cl |
| (5) | o-chlorophenyl | Br |
| (6) | o-chlorophenyl | I |
| (7) | 2-pyridyl | Cl |
| (8) | 2-pyridyl | Br |
| (9) | 2-pyridyl | I |

16. A compound according to claim 14 selected from the group comprising
    8-chloro-6-phenyl-1-thiomorpholino-4H-s-triazolo[4,3-a]-[1,4]benzodiazepine,
    8-bromo-6-phenyl-1-thiomorpholino-4H-s-triazolo[4,3-a]-[1,4]benzodiazepine, and 8-iodo-6-phenyl-1-thiomorpholino-4H-s-triazolo[4,3-a]-[1,4]benzodiazepine, or a pharmacologically acceptable acid addition salt thereof.

17. A compound according to claim 15 selected from the group comprising 8-chloro-6-phenyl-1-azetidino-4H-s-triazolo[4,3-a]-[1,4]benzodiazepine, 8-bromo-6-phenyl-1-azetidino-4H-s-triazolo[4,3-a]-[1,4]-benzodiazepine, and 8-iodo-6-phenyl-1-azetidino-4H-s-triazolo[4,3-a][1,4]-benzodiazepine, or a pharmacologically acceptable acid addition salt thereof.

18. A method according to any of claims 1 to 10, inclusive, wherein the mammal being treated is a human.

* * * * *

UNITED STATES PATENT OFFICE
CERTIFICATE OF CORRECTION

Patent No. 4,455,307            Dated 19 June 1984

Inventor(s) Jackson B. Hester, Jr.

It is certified that error appears in the above-identified patent and that said Letters Patent are hereby corrected as shown below:

Column 18, line 21, "1" should read -- I --.
Column 19, line 49, "$R_{14}$" should read -- $R_{114}$ --.

*Signed and Sealed this*

*Twelfth* Day of *November 1985*

[SEAL]

*Attest:*

DONALD J. QUIGG

*Attesting Officer*      *Commissioner of Patents and Trademarks*